United States Patent [19]

Griffin et al.

[11] 4,308,250
[45] Dec. 29, 1981

[54] SUSTAINED DRUG RELEASE DEVICE

[75] Inventors: Gerald J. L. Griffin, Ealing; Malcolm D. Brewer, Crawley, both of England

[73] Assignee: Beecham Group Limited, England

[21] Appl. No.: 214,778

[22] Filed: Dec. 9, 1980

Related U.S. Application Data

[62] Division of Ser. No. 92,178, Nov. 7, 1979, Pat. No. 4,268,497.

[30] Foreign Application Priority Data

Nov. 7, 1978 [GB] United Kingdom ............... 43555/78

[51] Int. Cl.³ .......................... A61K 9/70; A61J 3/00; A61J 3/07; A61K 9/52
[52] U.S. Cl. ..................................... 424/14; 128/260; 424/16; 424/27; 424/28
[58] Field of Search ...................... 424/14, 16, 27, 28; 128/260

[56] References Cited

U.S. PATENT DOCUMENTS

| | | | |
|---|---|---|---|
| 3,625,214 | 12/1971 | Higuchi | 128/260 |
| 3,832,252 | 8/1974 | Higuchi et al. | 156/86 |
| 3,844,285 | 10/1974 | Laby | 128/260 |
| 3,903,880 | 9/1975 | Higuchi et al. | 128/260 |
| 4,029,757 | 6/1977 | Mlodozeniec et al. | 424/27 |
| 4,031,200 | 6/1977 | Reif | 424/27 |
| 4,055,178 | 10/1977 | Harrigan | 128/260 |
| 4,072,551 | 2/1978 | Dabal et al. | 156/378 |
| 4,180,558 | 12/1979 | Goldberg et al. | 424/16 |
| 4,228,149 | 10/1980 | Brewer et al. | 424/14 |
| 4,268,497 | 5/1981 | Griffin et al. | 424/27 |

FOREIGN PATENT DOCUMENTS 2274 of 1869 United Kingdom ................ 424/14

Primary Examiner—Shep K. Rose
Attorney, Agent, or Firm—Jacobs & Jacobs

[57] ABSTRACT

A device for oral administration to a ruminant animal includes a veterinary medicament, such as an anthelmintic, uniformly dispersed throughout an erodable sheet comprising an ethylene-vinylacetate copolymer. The sheet is rolled up and stuck together with adhesive backed paper strips for administration, and unrolls in the rumen to take up a planar configuration which is retained in the rumen. The sheet may be placed within a plastics netting envelope to give more controlled erosion and release of medicament.

4 Claims, 3 Drawing Figures

SUSTAINED DRUG RELEASE DEVICE

CROSS-REFERENCE

This is a continuation of Ser. No. 92,178 filed Nov. 7, 1979, now U.S. Pat. No. 4,268,497.

This invention relates to a device giving sustained release of a veterinary medicament, a process for the preparation of such devices and a method for their use.

Ruminant animals, particularly cattle and sheep form an important group of animals which require periodic administration of veterinary medicaments for the treatment and alleviation of various conditions. For example, it is often desirable to treat such animals, either therapeutically or prophylactically, with anthelmintics. The repeated administration of such veterinary medicaments to animals at frequent time intervals is expensive and inconvenient.

U.K. Pat. No. 1318259 describes a number of devices for retaining slow release veterinary medicament formulations in the rumen over an extended period of time, and therefore achieving the desired result. This prolonged retention in the rumen is obtained by the devices having a relatively narrow first configuration which allows the devices to be administered per os to the ruminant, and a relatively broad second configuration which the devices assume or are caused to assume in the rumen thereby hindering or preventing their passage out of the rumen.

A typical example of such a device specifically described in the Patent is a plastic cylindrical capsule containing a detergent for the control of bloat in cattle. The capsule is 150 mm long and 30 mm wide (thereby allowing per os administration), and consists of two half-cylinders hinged along one edge. The hinges are made from rubber and are biased so that the two half-cylinders spring apart in the rumen and thus become too wide to pass out through the rumen or to be regurgitated through the oesophagus. Each half-cylinder contains a gel of ethyl cellulose containing the desired anti-bloat agent which is leached from the gel by the rumen fluids over an extended period of time. The hinges are constructed so that under the rumen conditions they pull away from the half-cylinders after effective release of the agent thereby facilitating regurgitation of the fragmented device.

Another example of such a device described in the Patent is a 'doughnut-shaped' ring made of an ethyl cellulose gel containing the desired anti-bloat agent. For administration the ring is deformed to an elongate configuration by means of a gelatin tape. In the rumen this tape dissolves and due to the resilience of the ring it reverts to its original configuration thereby preventing or hindering regurgitation thereof.

In our Offenlegungsschrift No. 28 24 288 it was disclosed that the desired sustained release of water soluble medicaments can be obtained by dispersing the medicament in a water insoluble polymer sheet, which sheet has a size and composition so that it can be constrained narrow enough for administration and yet move in the rumen to a position in which it is sufficiently broad to prevent regurgitation. This was particularly surprising as nowhere in U.K. Pat. No. 1318259 was this simple, cheap, strong and easily manufactured solution to the problem in any way suggested. In fact the only relevant use for polymers revealed in that patent was as a protective material to allow medicament incorporated therein and administered via the plastic cylindrical capsule to by-pass the rumen.

The device disclosed in our Offenlegungsschrift No. 28 24 288 depended for its release of medicament on the leaching out of water soluble medicament from an essentially water insoluble polymer matrix.

It is an object of this invention to provide a simple, cheap, strong and easily manufactured device which can be used to give a sustained release in the rumen of any medicament whatever its water solubility.

Accordingly the present invention provides a device for oral administration to a ruminant animal, comprising a veterinary medicament dispersed uniformly throughout an erodable sheet, the device being designed to be constrained into a first shape which allows oral administration and to assume in the rumen a second shape whereby it is retained therein. Preferably the erodable sheet comprises an erodable polymer. The sheet may be flexible to permit folding or rolling of the sheet into the first shape and unfolding or unrolling of the sheet into the second shape.

Examples of suitable medicaments include water soluble anthelmintics such as morantel, pyrantel, tetramisole, levamisole, butamisole, nitramisole and diethyl carbamazine and salts thereof, and salts of nitroxynil such as the N-ethyl glucamine salt; more suitably morantel, pyrantel, tetramisole, levamisole, or a salt thereof such as the hydrochloride. Piperazine and salts thereof may also be used. Preferred examples of water soluble anthelmintics include morantel or a salt thereof, such as salts with organic acids, e.g. citrate and tartrate, and levamisole or a salt thereof such as the hydrochloride. Sparingly soluble salts of the above water soluble anthelmintics may also be used, especially the pamoates.

Water insoluble and sparingly soluble anthelmintics may also be used. These suitably include albendazole, fenbendaxole, oxfendazole, oxybendazole, cambendazole, parbendazole, thiabendazole, febantel, thiophanate, diamphenethide, flukanide, flubendazole and mebendazole.

Also suitably any of the anthelmintics described in Offenlegungsschrift No. 28 36 690 and U.K. patent application No. 23071/78 (the disclosures of which patent Applications are substantially equivalent and are incorporated herein by reference) such as 1-[2-(4-chlorobenzylideneamino)-5-n-propylthiophenyl]-3-methoxycarbonyl-S-methylisothiourea of formula:

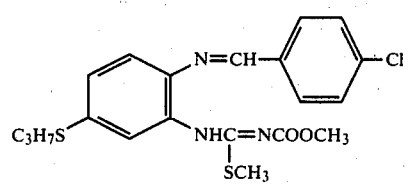

may be used.

Particularly suitably an anthelmintic for use in this device possesses a solubility in water at 39° C. of not more than 10%.

Other suitable medicaments include insecticides, methane inhibitors, coccidiostats, vitamins, mineral supplements (such as copper, selenium, cobalt or magnesium), growth promotors, and agents useful for the control of trypanosomiasis, babesiasis and diseases related thereto.

Suitably the medicament will represent 5 to 50% by weight of the sheet, more suitably 15 to 40% by weight.

The sheet may be made of any pharmaceutically acceptable material which is eroded in the rumen. This erosion may be caused by physical, chemical and/or biological factors in the rumen, such as the continual oscillation in the rumen, and contact with enzymes and the like in the rumen liquors; and it is this erosion of the sheet which yields the desired sustained release of the medicament dispersed uniformly throughout.

Preferably the sheet will be substantially entirely eroded away in 6 to 12 weeks in the rumen, thereby ensuring that the complete drug loading of the device is released in this time.

The precise nature of the erodable sheet is not of essential importance, and suitable materials may readily be determined by the skilled man either from his common general knowledge or by simple experiment, now that this utility for such materials has been discovered. However, we have found that often it will be convenient for the sheet to comprise a polymer. In such cases the polymer may be an erodable polymer, in which case the sheet may just consist of the polymer; or may be an inert polymer containing a biodegradable material to provide the necessary erodability for the sheet; or the erosion characteristics of a particular erodable polymer may be varied by incorporation therein of a biodegradable material.

We have found that suitable erodable sheets may be prepared from ethylene-vinyl acetate copolymers. Normally such copolymers will contain 40 to 70% vinyl acetate, preferably 60%. Examples of specific copolymers of this nature that may be used include ethylene-vinyl acetate copolymers Grades EY902, EY903, EY904, EY906 and EY907, which contain respectively 41%, 45%, 52%, 55% and 60% vinyl acetate respectively, which copolymers are available from U.S.I. Europe N.V., P.O. Box 529, B-2000 Antwerp, Belgium.

It is believed that preferred such copolymers for use in this invention include the EY904 Grade copolymer.

Other polymers which may be used include polyurethanes and polyvinylchlorides.

The erodability of a polymer sheet may suitably be varied, or provided, by blending therein biodegradable materials such as a starch, for example, corn, maize or potato starch; disaccharides such as lactose and wheat flour; celluloses such as methyl, ethyl and carboxymethyl cellulose; and proteins such as gelatine.

When present such biodegradable additives may suitably represent 10 to 50% by weight of the sheet, more suitably 20 to 40%.

In general with ethylenevinyl acetate copolymers the presence of a biodegradable material is preferred in order to ensure that the resultant sheet is erodable. However, we have found that in particular the EY904 Grade copolymer is satisfactorily eroded in the absence of any additives, although of course such additives may be included therein to vary the erosion rate if so desired.

The device of the invention must be capable of constraint into an orally administrable first shape and of assuming in the rumen a second shape retaining it therein.

The necessary constraint to the device to allow oral administration may be applied to the device by the throat of the animal itself. However, it is normally preferred that some constraining means is associated with the device to hold it in this position for administration purposes. The constraining means is chosen so that it is quickly removed in the rumen environment to allow the sheet to unfold once it is in the rumen in the manner of the invention. This constraining means may be any element that is able to hold the device in its constrained position for administration but is readily dissolved, destroyed, ruptured or otherwise removed by the rumen environment. Examples of suitable constraining means include gelatin string, gelatin tape, paper strips backed by water soluble adhesive, and water soluble paper.

The device is suitably formed into its constrained position by folding or rolling up the sheet.

The constrained device may be coated with a water soluble envelope to improve its appearance, for example of plastics or gelatine or like material, to ease administration and to enhance the storage stability of the device. Of course if desired this coating may itself provide the necessary constraint.

The ability of the device to assume the necessary second shape in the rumen may simply be provided by the natural resilience of the sheet causing it to unfold (assisted of course by the continual oscillation of the rumen), the sheet being of sufficiently great cross-section when unfolded to prevent rejection of the device from the rumen.

However, it will be appreciated that it may well be desired for such a substantial proportion of the sheet to erode during the effective life-time of the device that this erosion could well result in premature rejection of the device due to its substantial shrinkage in size; or for the sheet to be made of a non-resilient material. Accordingly in such circumstances the ability of the device to move from its first to its second shape (and retain this second shape for its effective life-time) may be provided by a resilient support member attached to or surrounding the sheet.

Conveniently this support member may be a sheet of resilient water insoluble polymer, having fused to one, or both, faces an erodable sheet, in which case it has been found that the resilient water insoluble polymer may suitably be an ethylene-vinyl acetate copolymer containing low levels of vinyl acetate, for example 5 to 30%, more suitably 20%. A particularly suitable copolymer for such use is believed to be ethylene-vinyl acetate copolymer Grade UE 631, which contains 20% vinyl acetate and is available from U.S.I. Europe N.V.

Alternatively, the support member may consist of netting or fibres of plastics materials, such as low density polyethylene, polypropylene and polyamides; sunk into, or fused against, erodable sheets.

In a highly preferred embodiment, the support member may take the form of an apertured, flexible envelope or bag which contains the erodable sheet. The envelope or bag may be constructed of plastics netting material which loosely contains the erodable sheet.

It will be appreciated that when the sheet of the device is highly erodable, then suitably a support member will be chosen which will give the sheet structural support.

Some of the materials, such are certain polymers, which it may be desired to use in the sheets of the device may be a little sticky. In such cases it may be advantageous to provide the sheet with a water soluble coat to ensure that the sheet fully unfolds when in the rumen. Examples of suitable coating materials include rice paper or other water soluble paper. Alternatively devices may be interleaved with water-absorbing sheets.

The size of the constituent parts of the device must be such that the device can be constrained small enough for administration, and in the rumen be large enough to prevent rejection. We have found that for sheep the erodable sheet is suitably of a thickness of 1 to 3 mm, a length of 5 to 8 cm, and a width of 3 to 5 mm. Similarly for cattle suitable dimensions of the sheet are respectively 2 to 4 mm, 7 to 10 cm, and 4 to 7 cm.

Suitably when present the support member has comparable dimensions. For example, when present a fused sheet support member suitably has a thickness of 0.5 to 1.5 mm and the erodable sheet to which it is fused suitably has a thickness of 0.5 to 2.0 mm.

The amount of medicament contained in the device will of course depend on the particular drug used, the type of animal, and the duration of release required. By way of example, with parbendazole suitably a device for a sheep would contain 0.5 to 2.0 gm., and a device for cattle would contain 2 to 5 gm., to give an effective drug release over about 12 weeks.

The devices will suitably weigh around 5 to 10 g. for sheep and around 6 to 20 g. for cattle.

The invention also provides a method of treatment of disorders in ruminant animals, which method comprises the oral administration to the animal of a device according to the invention.

It has been found the devices of the invention give a sustained release of medicament in the rumen thereby reducing the number of doses necessary to effect control or prophylaxis of disease.

The invention also provides a process for the preparation of the devices of the invention, which process comprises dispersing the medicament uniformly throughout an erodable sheet.

The exact manner in which this process is carried out will depend on the nature of the sheet material.

When the sheet material is a polymer, then the process may often suitably be carried out by softening pre-formed polymer and blending therein the medicament. For example the process may suitably be carried out by running a strip of polymer through a roll mill, which mill is heated to a temperature sufficient to soften the polymer but not to decompose the medicament. The medicament is then steadily added to the nip of the mill, and the strip of polymer recirculated until the required composition is achieved.

Any biodegradable materials necessary may be added to the polymer before, after or together with the drug.

The strip is then formed into a sheet of the desired dimensions, suitably by cutting. It may first, if necessary, be hot pressed to the desired thickness, for example between two polished steel plates.

The support member when present will be incorporated into the device in a manner which depends on the nature of the support. For example when the support is a polymer sheet, then it may merely be fused into position against the erodable sheet. When the support member is a flexible bag or envelope, its edges may be sealed round the erodable sheet to enclose completely the sheet.

The invention may be performed in various ways and two preferred embodiments are now described by way of example with reference to the accompanying drawings in which.

Figure 1:
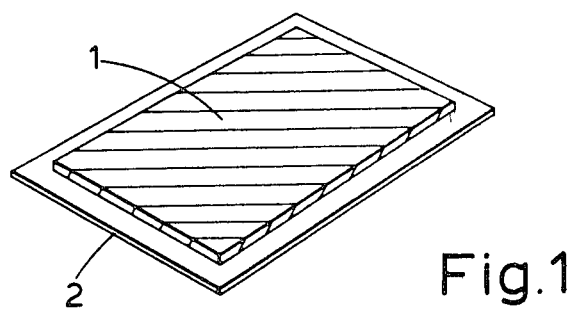
FIG. 1 is a perspective view of a device having an erodable sheet attached to a non-erodable sheet.

The device of FIG. 1 has an erodable sheet 1 consisting of an ethylene vinyl acetate copolymer (E.V.A.) Grade EY907 in which has been blended corn starch. The sheet 1 also contains parbendazole dispersed uniformly throughout; the parbendazole represents 20%, the EVA 45% and the corn starch 35% by weight of the device. The sheet 1 is approximately 2 mm. thick, 4 cm. wide and 6 cm. long.

The sheet 1 is attached face-to-face by a heat weld to a sheet 2 of insoluble ethylene vinyl acetate copolymer Grade U.E.631. This sheet 2 is approximately 1 mm. thick, 5 cm. wide and 7 cm. long.

Figure 2:
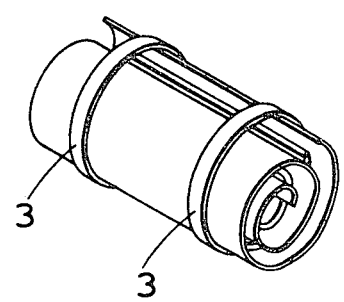
FIG. 2 is a perspective view of the device of FIG. 1 in its administration form.

FIG. 2 shows the device of FIG. 1 constrained into a first shape which allows oral administration to a sheep, which first shape is formed simply by rolling up the device and constraining it in this position, against the resilience of the two polymer sheets, with two strips of paper 3 gummed with a water soluble adhesive.

After administration per os to the sheep, the strips of paper 3 come unstuck, and the device unfolds from its first shape (as shown in FIG. 2), under the influence of the polymer resilience and aided by the oscillation experienced in the sheep's rumen, to assume a substantially flat second shape (as shown in FIG. 1) whereby the device is retained in the rumen.

Figure 3:
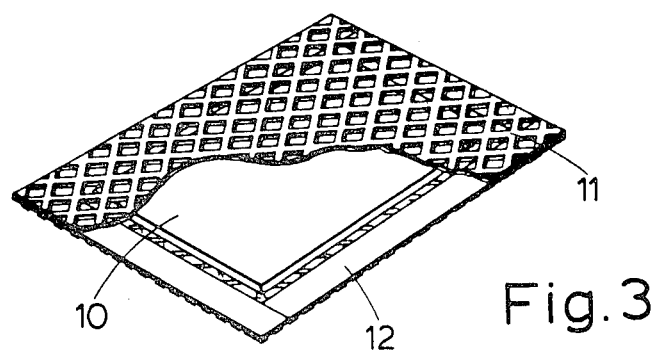
FIG. 3 is a perspective view of a device having an erodable sheet contained in a plastics netting envelope.

The device of FIG. 3 has an erodable sheet 10 consisting of an ethylene vinyl acetate copolymer (EVA) Grade EY 904 in which has been blended methyl cellulose. The sheet 10 also contains parbendazole dispersed uniformly throughout. The percentage composition of the sheet 10 is from 25 to 60% EVA, 20 to 50% parbendazole and 20 to 40% methyl cellulose. Gelatine, starch or sodium alginate may be used in place of methyl cellulose as a biodegradable filler. Other Grades of EVA may also be used, such as EY 902, EY 903 and EY 906. The sheet 10 is approximately 0.15 mm thick, 4 cm wide and 6 cm long, and is contained within a plastics netting envelope 11 of width approximately 4 cm and length 7 cm. The netting envelope 11 is sealed along its edges by polythene strips 12 heat welded to the netting.

The device of FIG. 3 can be rolled up into a similar configuration as shown in FIG. 2 for administration per os to the sheep, and it will unroll to its planar configuration in the rumen.

The netting envelope permits the rumen liquors to erode gradually the sheet 10 in a controlled manner, and helps to prevent a premature break up of the sheet 10 into smaller pieces which might then be excreted from the rumen at too early a stage.

The following Examples illustrate further features of the invention:

EXAMPLE 1

The following method was used to prepare a sheet containing 20 gm. parbendazole, 60 gm. ethylene vinyl acetate copolymer (E.V.A.) grade EY 907, and 20 gm. corn starch.

The E.V.A. was fluxed on a 25×7 cm. 2-roll mill and when it was running as a smooth hide, the corn starch and then the parbendazole were steadily added to the nip. The hide was cut and turned many times to ensure uniformity. The machine was oil heated to a temperature of 100° C., sufficient to flux the resin but not so high that the compound stuck to the rolls or the drug decomposed.

From this 100 g. mixture, two 50 g. portions of the rough hide from the mill were hot-pressed into sheets 2 mm. thick, within a steel frame (internal dimensions 15.5×10.5 cm.), between polished steel plates for two minutes at a pressure of 280 kg. cm-2 and temperature of 100° C. Melinex polyester foil was used as a facing material to enable the copolymer to be released easily from the press.

Samples from these sheets were then cut, as 6×4 cm. rectangles.

EXAMPLE 2

Erodable sheets having the compositions given in Table 1 were prepared in the manner of Example 1, sized 6×4×0.2 cm., and were heat welded on the face to sheets of pure EVA (grade UE 631) of size 7×5×0.1 cm. Samples of each device were dosed orally to 6 sheep. Two animals were killed, 1, 3 and 6 weeks after dosing.

Recovered devices were washed and dried at 37° C., then weighed. Three discs (13 mm. diameter) were taken from each device recovered and processed in the following way:

Each disc was weighed, cut up into small pieces and left in known volumes (50 ml.) of 2% acid (HCl) alcohol for 7 days at 34° C.

The drug released from these discs was assayed using a Perkin Elmer spectrophotometer (Model 137 UV) taking the difference between absorption readings at 289° A and 304° A, and following calibration with standard drug solutions.

The results given in the Table below show the percentage parbendazole loss (using pre and post treatment values) from a number of devices recovered from sheep at different time intervals.

The results indicate that continuous release of active agent is obtained under field conditions for periods of at least 6 weeks.

TABLE 1

| Erodable sheet composition | % Parbendazole loss | | |
|---|---|---|---|
| | 1 week | 3 weeks | 6 weeks |
| 70% EY 907<br>30% Parbendazole | 0 | 10.0 | 20.6 |
| 80% EY 907<br>20% Parbendazole | 8.3 | 13.4 | 13.4 |
| 50% EY 907<br>30% Parbendazole<br>20% Starch | 5.5 | 9.4 | 13.0 |
| 60% EY 907<br>20% Parbendazole<br>20% Starch | 6.9 | 10.3 | 20.8 |
| 40% EY 907<br>20% Parbendazole<br>40% Starch | 2.5 | 12.2 | 17.0 |
| 45% EY 907<br>20% Parbendazole<br>35% Starch | 16.5 | 28.7 | 44.3 |
| 40% EY 907<br>40% Parbendazole<br>20% Starch | 1.8 | 12.5 | 16.6 |
| 40% EY 907<br>30% Parbendazole<br>30% Starch | 2.2 | 10.2 | 10.0 |

EXAMPLE 3

Erodable sheets 10 having the compositions given in Table 2 below were prepared in a similar manner to Example 1, but using methyl cellulose in place of corn starch and EVA Grade 904 in place of Grade 907. Plastics netting envelopes were made from a low density polythene netting, "Netlon" (Trade Mark), having holes approximately 3 mm ×3 mm in size. Squares of this material, 27 cm ×27 cm in size, were pressed between steel plates at 100° C. for 2 minutes at 20 tonnes in a conventional electric press. After pressing, the netting was approximately 0.35 to 0.4 mm thick, with holes of approximately 2 mm in diameter. Each erodable sheet 10 was placed between two sheets of pressed netting 7 cm ×4 cm in size, and the edges of the two sheets of netting was sealed with an electric heat sealer. To strengthen the seal a strip of polyethylene was heat welded between the two edges of the netting.

The plastics netting envelopes 11 containing the sheets 10 were rolled up, secured with paper strips 3 as shown in FIG. 2, and dosed orally to sheep. The envelopes were recovered 1, and 3 weeks after dosing and the percentage parbendazole losses given in Table 2 were found in a similar way as in Example 2. The results in Table 2 indicate that continuous release of active agent is obtained under field conditions for periods of at least 3 weeks.

TABLE 2

| Erodable Sheet Composition | Parbendazole Loss | |
|---|---|---|
| | 1 week | 3 weeks |
| 40% EY 904<br>30% Parbendazole<br>30% Methyl Cellulose | 0.7 | 12.9 |
| 30% EY 904<br>40% Parbendazole<br>30% Methyl Cellulose | 9.5 | 51.3 |
| 40% EY 904<br>35% Parbendazole<br>25% Methyl Cellulose | 4.9 | 15.9 |
| 45% EY 904<br>30% Parbendazole<br>25% Methyl Cellulose | 0 | 11.6 |
| 50% EY 9.4<br>25% Parbendazole<br>25% Methyl Cellulose | 3.0 | 17.5 |

We claim:

1. A device for administration of a veterinary medicament to a ruminant comprising a first resilient sheet of an erodable ethylene-vinyl acetate copolymer in which said medicament is uniformly dispersed and a second resilient, support sheet of a water insoluble polymer, said second sheet being at least dimensionally coextensive with said first sheet and to which said first sheet is attached, said device being of a size and composition such that it is capable of constraint in a rolled-up configuration permitting oral administration and of a subsequent assumption of an unrolled configuration when unconstrained in the rumen.

2. A device according to claim 1 wherein the medicament constitutes 15 to 40% by weight of said first sheet.

3. A device according to claim 2 wherein the medicament is an anthelmintic.

4. A device according to claim 2 wherein said second support sheet consists of ethylene-vinyl acetate copolymer.

* * * * *